United States Patent [19]
Sinclair

[11] Patent Number: 5,877,184
[45] Date of Patent: Mar. 2, 1999

[54] MACROLIDES HAVING IMMUNOSUPPRESSIVE ACTIVITY

[75] Inventor: Peter J. Sinclair, Highland Park, N.J.

[73] Assignee: Merck & Co., Inc., Rahway, N.J.

[21] Appl. No.: 882,978

[22] Filed: Jun. 26, 1997

Related U.S. Application Data

[60] Provisional application No. 60/023,367, Aug. 6, 1996.
[51] Int. Cl.[6] ........................ C07D 491/16; A61K 31/345
[52] U.S. Cl. ........................ 514/291; 514/411; 514/183; 540/456
[58] Field of Search ............................ 540/456; 514/291, 514/411, 183

[56] References Cited

U.S. PATENT DOCUMENTS

| | | | |
|---|---|---|---|
| 5,189,042 | 2/1993 | Goulet et al. | 514/291 |
| 5,344,925 | 9/1994 | Goulet et al. | 540/456 |
| 5,349,061 | 9/1994 | Sinclair et al. | 540/456 |
| 5,561,137 | 10/1996 | Or et al. | 514/291 |
| 5,563,172 | 10/1996 | Wagner et al. | 540/456 |

FOREIGN PATENT DOCUMENTS

| | | |
|---|---|---|
| 2245891 | 1/1992 | United Kingdom . |
| 2246568 | 2/1992 | United Kingdom . |

*Primary Examiner*—Mukund J. Shah
*Assistant Examiner*—Deepak R. Rao
*Attorney, Agent, or Firm*—Mollie M. Yang; David L. Rose

[57] ABSTRACT

Macrolides of the general structural Formula I:

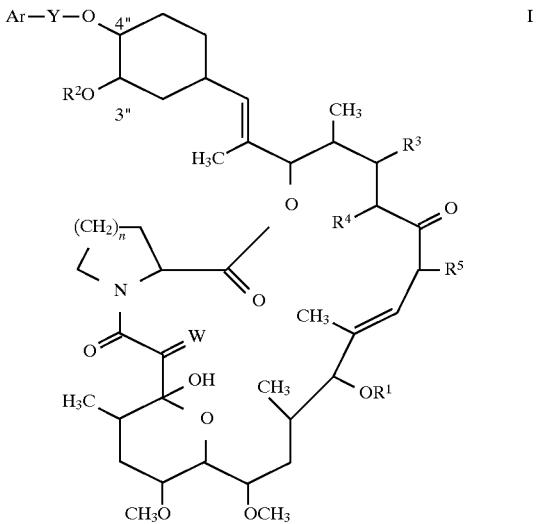

are immunosuppressants useful in a mammalian host for the treatment of autoimmune diseases, infectious diseases and/or the prevention of rejection of foreign organ transplants and/or related afflictions, diseases and illnesses.

8 Claims, No Drawings

MACROLIDES HAVING IMMUNOSUPPRESSIVE ACTIVITY

CROSS REFERENCE TO RELATED APPLICATIONS

This application is based on, and claims priority from, provisional application 60/023,367 filed on Aug. 6, 1996.

SUMMARY OF THE INVENTION

The present invention is related to C-20 hydroxy macrolides which are useful in a mammalian subject for the treatment of autoimmune diseases (such as juvenile-onset or recent-onset diabetes mellitus, multiple sclerosis, and rheumatoid arthritis, liver disease, posterior uveitis, allergic encephalomyelitis, and glomerulonephritis), immunodepression, infectious diseases and/or the prevention of rejection of foreign organ transplants, (e.g. bone marrow, kidney, liver, heart, skin, small-bowel, and pancreatic islet-cell transplants, including xeno transplants), the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia areata), male pattern alopecia, alopecia senilis, reversible obstructive airways disease, particularly asthma, inflammation of mucosa and blood vessels, cytomegalovirus infection, multidrug resistance, idiopathic thromboytopenic purpura, Behcet's syndrome, conjunctivitis, Crohn's disease, Mooren's ulcer, uveitis, severe intraocular inflammation and/or hepatic injury associated with ischemia. The present compounds are further useful in combination with a 5α-reductase inhibitor, a cyclosporin, a potassium channel opener or a phospholipid in a mammalian host for the treatment of baldness, especially male pattern alopecia, female pattern alopecia, alopecia senilis, or alopecia areata. In addition, some of the compounds of this invention may have antagonistic properties and so have utility in the reversal of immunosuppressive activity and/or diminishing the toxicity of other immunosuppressive agents.

This invention also relates to pharmaceutical compositions containing the compounds, and to a method of use of the present compounds and other agents for the treatment and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900506) (FK-506) (L-679,934), 17-ethyl-1,14-dihydroxy-12-[2'-(4"-hydroxy-3"-methoxycyclohexyl)-1'-methyl-vinyl]-23,25-dimethoxy-13,19,21,27-tetramethyl-11,28-dioxa-4-azatricyclo[22.3.1.0$^{4,9}$]-octacos-18-ene-2,3,10,16-tetraone (FR-900520) and related compounds which are the starting materials for the preparation of the compounds described. The synthetic preparation of the aforementioned starting material (FR-900506) has been reported (*J. Am. Chem. Soc.*, 1989, 111, 1157). A Sandoz U.S. patent (U.S. Pat. No. 5,011,844) and European patent application (EPO Publication No. 0,356, 399) disclose stereoisomers of FR-900506 and derivatives at the 17-position. Fisons European and WIPO patent applications (EPO Publication No. 0,323,042 and PCT Publication No. WO89/05304) disclose various derivatives of FR-900506, FR-900520 and related compounds. A Sandoz European patent application (EPO Publication No. 0,437,680) discloses chloro, bromo, iodo and azido derivatives of FR-900506, FR-900520 and related compounds. A Merck European patent application (EPO Publication No. 0,428,365) discloses various amino derivatives of FR-900506, FR-900520 and related compounds. A Fujisawa UK patent application (UK Publication No. GB 2,245,891A) discloses various aryl(lower alkyl) and heteroaryl derivatives of FR-900506, FR-900520 and related compounds. Merck WIPO patent applications (PCT Publication Nos. WO 93/05058 & WO 93/05059) disclose various heteroaryl derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons World patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthitis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmul. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117), multidrug resistance (M. Naito, et al., *Cancer Chemother. Pharmacol.*, 1992, 29, 195–200), inflammation of mucosa and blood vessels (PCT Publication WO 91/17754), cytomegalovirus infection (UK Publication GB 2,247,620A), and idiopathic thrombocytopenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, type 2 adult onset diabetes, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, tacrolimus, FR-900506, FK-506,

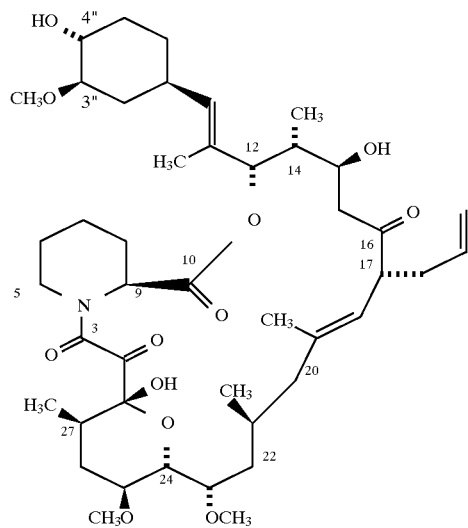

(17-allyl-1,14-dihydroxy-12-[2'-(4"-hydroxy-3"-methoxycyclohexyl)-1'-methylvinyl]-23,25-dimethoxy-13, 19,21,27-tetramethyl-11,28-dioxa-4-azatricyclo-[22.3.1.0$^{4,}$ $_9$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthitis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmol. Vis. Sci.,* 1988, 29, 1265–71), hepatic injury associated with ischemia (M. Sakr, et al., *Life Sci.,* 1990, 47, 687–91) allergic encephalomyelitis (K, Deguchi, et al., *Brain Nerve,* 1990, 42, 391–97), glomerulonephritis (J. McCauley, et al., *Lancet,* 1990, 335, 674), systemic lupus erythematosus (K. Takabayashi, et al., *Clin. Immunol. Immunopathol.,* 1989, 51, 110–117) multidrug resistance (M. Naito, et al., *Cancer Chemother. Pharmacol.,* 1992, 29, 195–200), inflammation of mucosa and blood vessels (PCT Publication WO 92/17754), cytomegalovirus infection (UK Publication GB 2,247,620A), and idiopathic thrombocytopenic purpura and Basedow's disease (PCT Publication WO 91/19495).

Baldness or alopecia, in addition to male pattern alopecia, female pattern alopecia, and alopecia senilis, includes alopecia areta, and further, diseases accompanied by basic skin lesions such as cicatrix or infectious tumors, or accompanied by systemic disorders, for examples, an internal secretion abnormality or nutritional disorder.

In regard to alopecia areata, it is considered that an autoimmune phenomenon participates therein, and therefore, the administration of a substance having an immunosuppressive action can have therapeutical effect on alopecia areata.

The causes of human pattern alopecia (also called "androgenic alopecia") and alopecia senilis are considered to be: an activation of male hormones at organs such as hair roots and the sebum gland; a lowering in the amount of blood reaching the hair follicles; a scalp abnormality caused by an excessive secretion of sebum, a formation or peroxides, or a propagation of bacteria; genetic; causes; and aging.

The compound minoxidil (6-amino-1,2-dihydro-1-hydroxy-2-imino-4-piperidinopyrimidine) was approved by the FDA for the treatment of male pattern baldness in August 1988. Minoxidil was also approved by the FDA for the treatment of female androgenetic alopecia on Aug. 13, 1991. The preparation of minoxidil is described in U.S. Pat. Nos. 3,382,247, 3,644,364 and 4,098,791. Upjohn United States Patents (U.S. Pat. Nos. 4,139,619 and 4,596,812) discloses the use of minoxidil in the topical treatment of human baldness. Similarly, an Upjohn United States Patent (U.S. Pat. No. 5,026,691) discloses the use of minoxidil and an antiinflammatory agent for the treatment of patterned male and female alopecia. Japanese patent Kokai 61-260010 states that topical minoxidil formulations containing other specified agents may be prepared. An Upjohn WIPO patent application (PCT Publication No. WO 92/09259) discloses a method and composition for promoting hair growth in mammals comprising the administration of a potassium channel opener and an androgen receptor blocker. A University of Miami WIPO patent application (PCT Publication No. WO 92/12703) discloses a method of stimulating hair growth comprising the topical application of a phospholipid.

Merck U.S. Pat. No. 4,760,071 discloses the 5α-reductase inhibitor 17β-(N-tert-butylcarbamoyl)-4-aza-5α-androst-1-en -3-one. Harris, et al., (*Proc. Natl. Acad. Sci. USA*, 89, 10787–10791 (Nov. 1992)) and Melin, et al. (*J. Steroid Biochem, Molec. Biol.*, 44(2), 121–131 (1993)) disclose the use of scalp-selective 5α-reductase inhibitors in the treatment of male pattern baldness, acne and hirsutism.

DETAILED DESCRIPTION OF THE INVENTION

A. Scope of the Invention

The novel compound of this invention has structural Formula I:

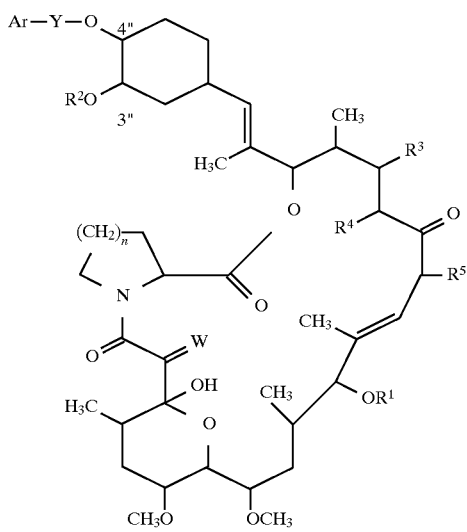

or a pharmaceutically acceptable salt thereof, wherein:

Ar is phenyl, naphthyl or biphenyl, each optionally substituted with 1 to 3 groups independently selected from X, $R^1$ is hydrogen, $C_{1-6}$ alkyl, $C_{1-6}$ alkanoyl, aroyl or aryl-$C_{1-6}$ alkanoyl;

$R^2$ is hydrogen or methyl;

$R^3$ is hydrogen or —$OR^1$;

$R^4$ is hydrogen, or $R^3$ and $R^4$ taken together form a double bond;

$R^5$ is methyl, ethyl, propyl or allyl,

W is O or (H, OH);

X is:
(b) $C_{1-7}$ alkyl,
(c) $C_{2-6}$ alkenyl,
(d) halogen,
(e) —$(CH_2)Hd$ m—$NR^6R^7$, wherein $R^6$ and $R^7$ are independently hydrogen or C1–10 alkyl, or R6, R7 and the nitrogen atom to which they are attached together form an unsubstituted or substituted 3–7-membered saturated heterocyclic ring which can include one or two additional heteroatoms independently selected from the group consisting of O, $S(O)_m$, $NR^{14}$, wherein $R^{14}$ is hydrogen or $C_{1-6}$ alkyl, and m is 0 to 2,
(f) —CN,
(g) —CHO,
(h) —$CF_3$,
(i) —$S(O)_mR^8$, wherein $R^8$ is hydrogen, $C_{1-6}$alkyl, trifluoromethyl, or phenyl, and m is as defined above,
(l) —$CONR^6R^7$, wherein $R^6$ and $R^7$ are as defined above,
(m) $R^9O(CH_2)_m$— wherein $R^9$ is hydrogen, $C_{1-3}$ alkyl, hydroxy-$C_{2-3}$alkyl, trifluoromethyl, phenyl or naphthyl and m is as defined above,
(n) —$CH(OR^{12})(OR^3)$, wherein $R^{12}$ and $R^{13}$ are $C_{1-3}$ alkyl or taken together form an ethyl or propyl bridge,
(o) $R^9C(O)O(CH_2)_m$— wherein $R^9$ and m are as defined above, and
(p) $R^9OC(O)(CH_2)_m$— wherein $R^9$ and m are as defined above, and
(q) —$OR^8$;

or any two adjacent X can be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl;

Y is a bond, $C_{1-10}$ alkyl, $C_{3-10}$ alkenyl or $C_{3-10}$ alkynyl, wherein said alkyl, alkenyl and alkynyl are optionally substituted with 1 or 2 groups independently selected from —$OR^1$ and oxo; and n is 1 or 2, or a pharmaceutically acceptable salt thereof.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

When any variable occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkanoyl" is intended to include those alkylcarbonyl groups of specified number of carbon atoms, which are exemplified by formyl, acetyl, propanoyl and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable; and "aralkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

One embodiment of the present invention encompasses the compounds of Formula I wherein Ar is phenyl or naphthyl, each optionally substituted with 1 to 3 groups independently selected from X; and Y is a bond, $C_{1-10}$ alkyl or $C_{3-10}$ alkenyl wherein said alkyl and alkenyl are optionally substituted with 1 or 2 groups independently selected from —$OR^1$ and oxo.

Another embodiment of the present invention encompasses the compounds of Formula I wherein $R^5$ is ethyl or allyl.

In the present invention it is preferred that in compounds of Formula I Ar is phenyl or naphthyl, each optionally substituted with 1 to 3 groups independently selected from X; $R^4$ is hydrogen; $R^5$ is ethyl or allyl; W is O; Y is a bond, $C_{1-10}$ alkyl or $C_{3-10}$ alkenyl wherein said alkyl and alkenyl are optionally substituted with 1 or 2 groups independently selected from —$OR^1$ and oxo; and n is 2.

In another preferred embodiment compounds of formula I have the stereochemistry as shown below:

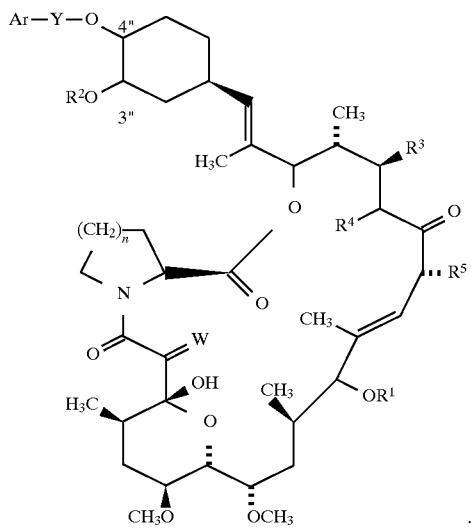

B. Preparation of Compounds Within the Scope of the Present Invention

The starting materials for the preparation of the compounds of this invention are represented by Formula II:

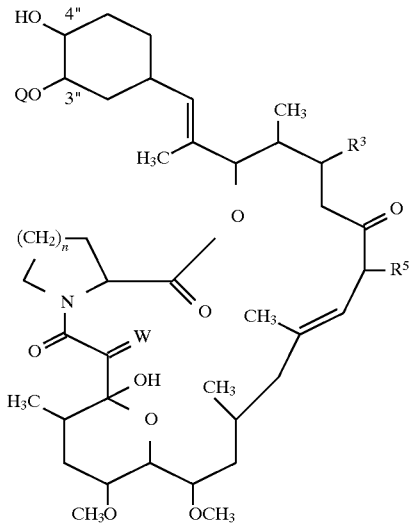

wherein:
Q is hydrogen or methyl;
W is O or (H, OH);
$R^3$ is hydrogen, hydroxy, or $C_1$–$C_6$ alkoxy;
$R^4$ is hydrogen, or $R^3$ and $R^4$ taken together form a double bond;
$R^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042; EPO Publication No. 0,356,399; PBJ Disclosure 63-17884: *J. Am. Chem. Soc.*, 1987, 109, 5031; and *J. Antibiotics*, 1987, 40, 1249). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, No. 7238 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where Q is methyl, W is O, $R^3$ is hydroxyl, $R^4$ is hydrogen, $R^5$ is allyl and n is 2; (B) where Q is methyl, W is O, $R^3$ is hydroxyl, $R^4$ is hydrogen, $R^5$ is ethyl and n is 2; (C) where Q is methyl, W is O, $R^3$ is hydroxyl, $R^4$ is hydrogen, $R^5$ is methyl and n is 2; and (D) where Q is methyl W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1–3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxy at C-4" may also be protected. In addition, the hydroxy of $R^3$ may be reduced to a hydrogen or eliminated to form a double bond with $R^4$ (by methods disclosed in U.S. Pat. No. 4,894,366 or EPO Publication No. 0,323,042 or EPO Publication No. 0,413,532). The carbonyl of W may be reduced to the alcohol by methods disclosed in EPO Publication No. 0,323,042 or by methods disclosed in U.S. Pat. No. 5,064,835 or in EPO Publication No. 0,445,975.

The methyl of Q as produced may be replaced with hydrogen or demethylated and subsequently protected as desired, if necessary. This demethylation of compounds wherein Q is methyl may be carried out in a fermentation reaction using the compounds of Formula II as a feedstock. For instance, compound A named under Formula II above may be demethylated at Q above by using the microorganism Actinomycetales ATCC No. 53771 (described in U.S. Pat. No. 4,981,792, issued Jan. 1, 1991) or by using the microorganism *Streptomyces tsukubaensis*, No. 9993 (described in EPO Publication No. 0,353,678). Similarly, compound B named under Formula II above may be demethylated at Q above using the microorganism *Actinoplanacete* sp. ATCC No. 53771 (described in EPO Publication No. 0,349,061). In addition the compound of Formula II wherein Q is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication 0,388,152) Similarly, the compound of Formula II wherein Q is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication 0,388,153). Also, the compound of Formula II wherein Q is hydrogen, $R^3$ is hydroxy, $R^4$ is hydrogen, $R^5$ is allyl, W is 0 and n is 2 and the compound of Formula II wherein the C-3"position is oxo (keto), $R^3$ is hydroxy, $R^4$ is hydrogen, $R^5$ is allyl, W is 0 and n is 2 may be produced directly by fermentation using the microorganism *Streptomyces tsukubaensis*, No. 9993 (described in EPO Publication No. 0,353,678). The hydroxy of C-3" may be protected by methods similar to those known for the protection of the hydroxyl groups of $R^3$ and/or C-4", for example as disclosed in U.S. Pat. No. 4,894,366.

The C-20 hydroxyl group can be introduced by treating a suitably protected compound of formula II with selenium dioxide in an aqueous alcoholic solvent such as 95% ethanol in the presence of pyridine at solvent reflux temperature.

Suitable protecting groups for hydroxyl include those groups well known in the art such as:

1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be C1–C4 alkylthiomethyl and the most preferred one may be methylthiomethyl; trisubstituted silyl such as tri(lower) alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$–$C_4$)alkylsilyl and $C_1$–$C_4$ alkyl- diphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like. Compounds A, B, C and D of Formula II, organisms to produce the same, conditions of fermentation, separation techniques, and chemical modification of the products are fully described in U.S. Pat. No. 4,894,366, issued Jan. 16, 1990 and U.S. Pat. No. 4,929,611, issued May 29, 1990.

The 5α-reductase inhibitor may be an inhibitor of 5α-reductase isozyme 1 and/or 5α-reductase isozyme 2. A preferred 5α-reductase inhibitor is finasteride. It is also preferred that the 5α-reductase inhibitor be selective for the scalp-associated enzyme 5α-reductase isozyme 1.

4-Aza steriod compounds are known in the art as 5α-reductase inhibitors. For example, See U.S. Pat. Nos. 2,227,876, 3,239,417, 3,264,301 and 3,285,918; French Patent No. 1,465,544; Doorenbos and Solomons, *J. Pharm. Sci.* 62, 4, pp. 638–640 (1973); Doorenbos and Brown, *J. Pharm. Sci.*, 60, 8, pp. 1234–1235 (1971); and Doorenbos and Kim, *J. Pharm. Sci.* 63, 4, pp. 620–622 (1974).

In addition, U.S. Pat. Nos. 4,377,584, 4,220,775, 4,859, 681, 4,760,071 and the articles *J. Med. Chem.* 27, p. 1690–1701 (1984) and *J. Med. Chem.* 29, 2998–2315 (1986) of Rasmusson, et al., U. S. Pat. No. 4,845,104 to Carlin, et al., and U.S. Pat. No. 4,732,897 to Cainelli, et al. described 4-aza 17β-substituted-5α-androstan-3-ones useful in the treatment of DHT-related hyperandrogenic conditions.

Cyclosporin may be prepared essentially as described in U.S. Pat. No. 4,117,118 or by R. Wenger, *Transplant. Proc.*, 15 (4), Suppl. 1, 2230 (1983) and is available from Sandoz Pharmaceuticals, East Hanover, N.J.

The potassium channel opener may be minoxidil, cromakalim, pinacidil, a triazine compound, a thiane-1-oxide, or other compounds.

Chemically minoxidil is 6-amino-1,2-dihydro-hydroxy-2-imino-4-piperidinopyrimidine and analogs thereof. The preparation of these compounds are described in U.S. Pat. Nos. 3,382,247, 3,461,461 and 3,644,364 and J. M. McCall, et al., *J. Org. Chem.*, 40, 3304 (1975). Related compounds are sulfoxypyrimidinium, -pyridinium, and -triazinium which are described in U.S. Pat. No. 4,287,338. The term "minoxidil" includes any of the various forms of 6-amino-1,2-dihydro-hydroxy-2-imino-4-piperidinopyrimidine, derivatives and analogs thereof. Minoxidil is distributed by The Upjohn Company, Kalamazoo, Mich.

Chemically cromakalim is (3S-trans) 3,4-dihydro-3-hydroxy-2,2-dimethyl-4-(2-oxo-1-pyrrolidinyl)-2H-1-benxopyran-6-carbonitrile. Cromakalim is distributed by SmithKline Consumer Products, Philadelphia, Pa.

Pinacidil is chemically, N-cyano-N'-4-pyridinyl-N"-(1,2, 2-trimethylpropyl)-guanidine monohydrate. The preparation of pinacidil is described in U.S. Pat. No. 4,057,636 and is distributed by Eli Lilly and Company, Indianapolis, Ind.

S-Triazine compounds or 2,6-diamino-4-substituted-s-triazine-1-oxides are described in U.S. Pat. No. 3,270,014 assigned to The Upjohn Company, Kalamazoo, Mich.

Thiane-1-oxide compounds are described in U.S. Pat. No. 4,568,682 assigned to Rhone-Poulenc Sante, Courbevoie, France. Other derivatives include those disclosed in patent applications EP 0,321,274 A, EP 0,321,273 A, and EP 0,326,297 A.

Other potassium channel openers include pyranopyridine derivatives described in patent applications GB 2,204,868 A and benzopyran derivatives described in patent publications GB 2,204,868 A, EP 0,314,446 A2, EP 0,339,562 A, EP 0,340,718 A, EP 0,337,179, AU A 18556/88, JA 1,294,677 A, EP 0,359,537 A, and U.S. Pat. No. 4,900,752.

The phospholipids used herein may be obtained from commercial sources. The phospholipids may also be isolated from natural sources (for example, egg yolk, soybean or other oily seed including safflower, sunflower and olive, and brain tissue) or may be produced synthetically. In either case, known techniques can be used for purification of the phospholipids (see, for example, *J. of American Oil Chemists Soc.* 42:53–56 (1965)).

The novel processes for preparing the novel compounds of the present invention are illustrated as follows, wherein $R^1$, $R^2$, $R^3$, $R^5$, Q, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

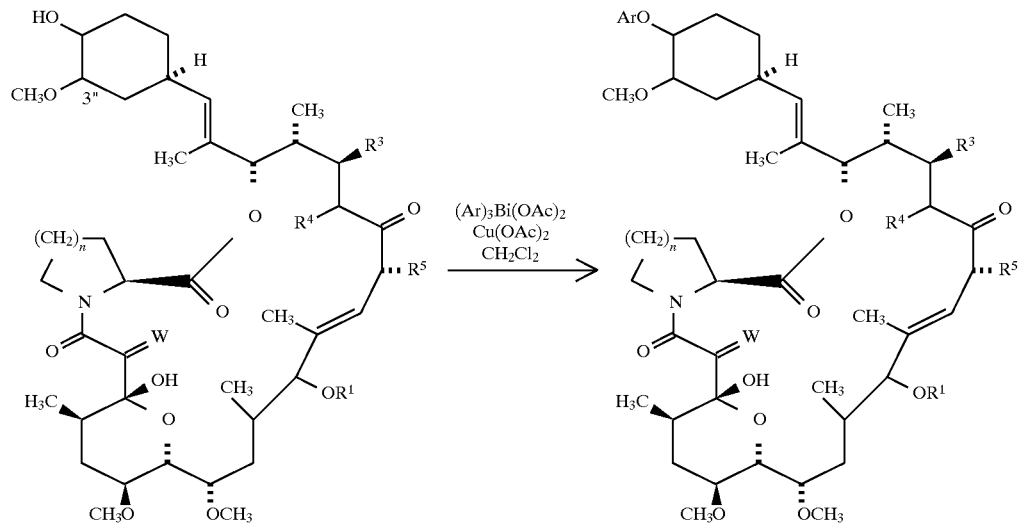

REACTION SCHEME B

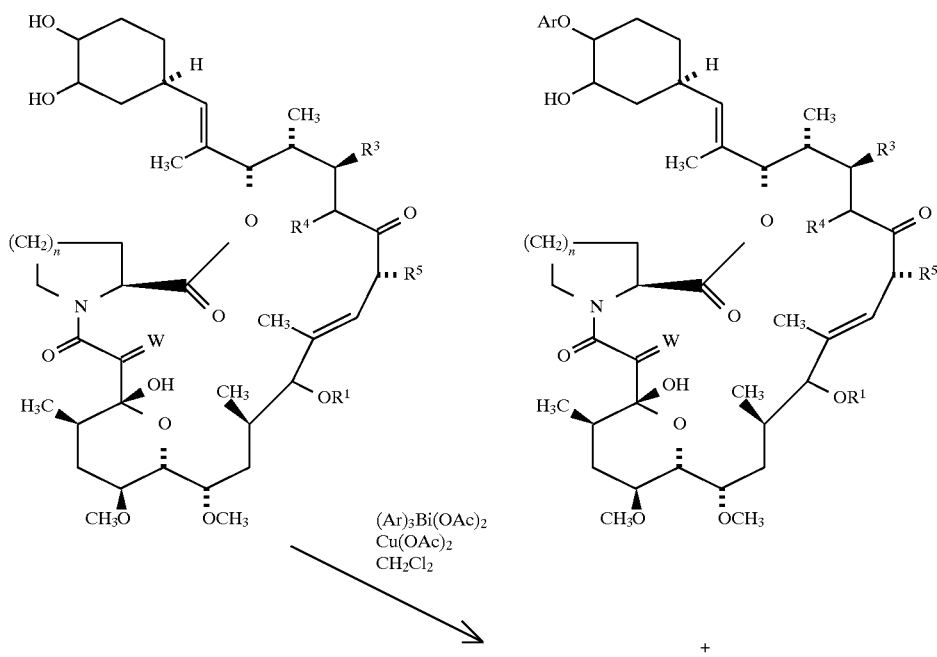

-continued
REACTION SCHEME B
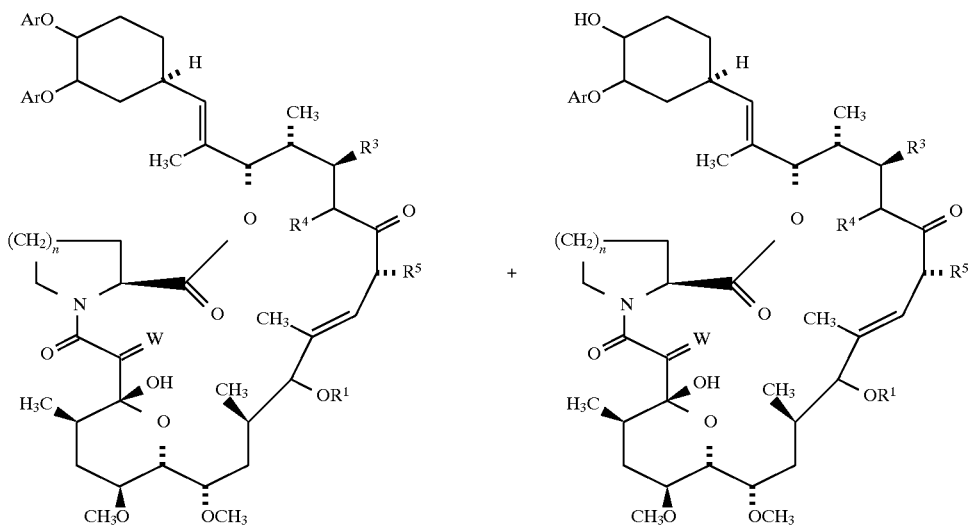
REACTION SCHEME C
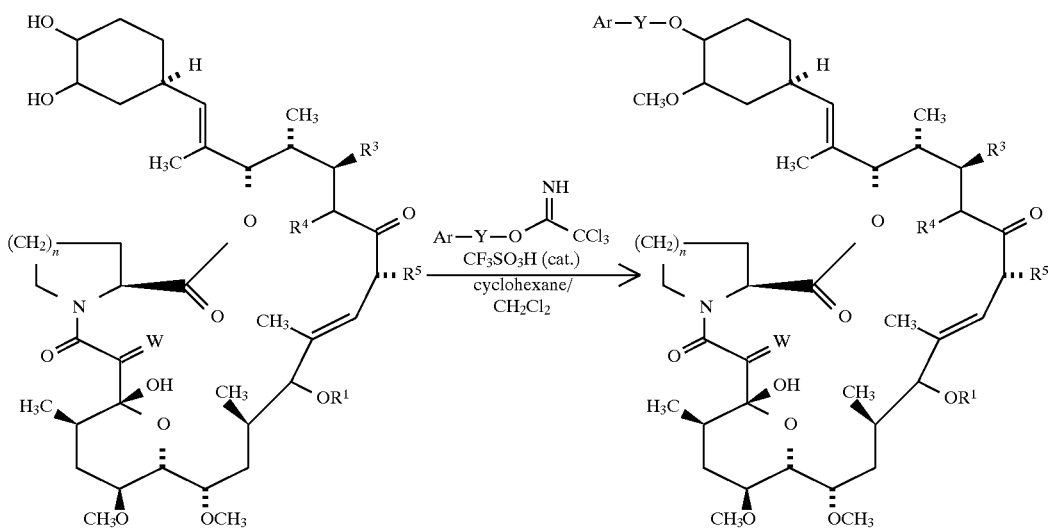
(Y is other than a bond)

REACTION SCHEME D
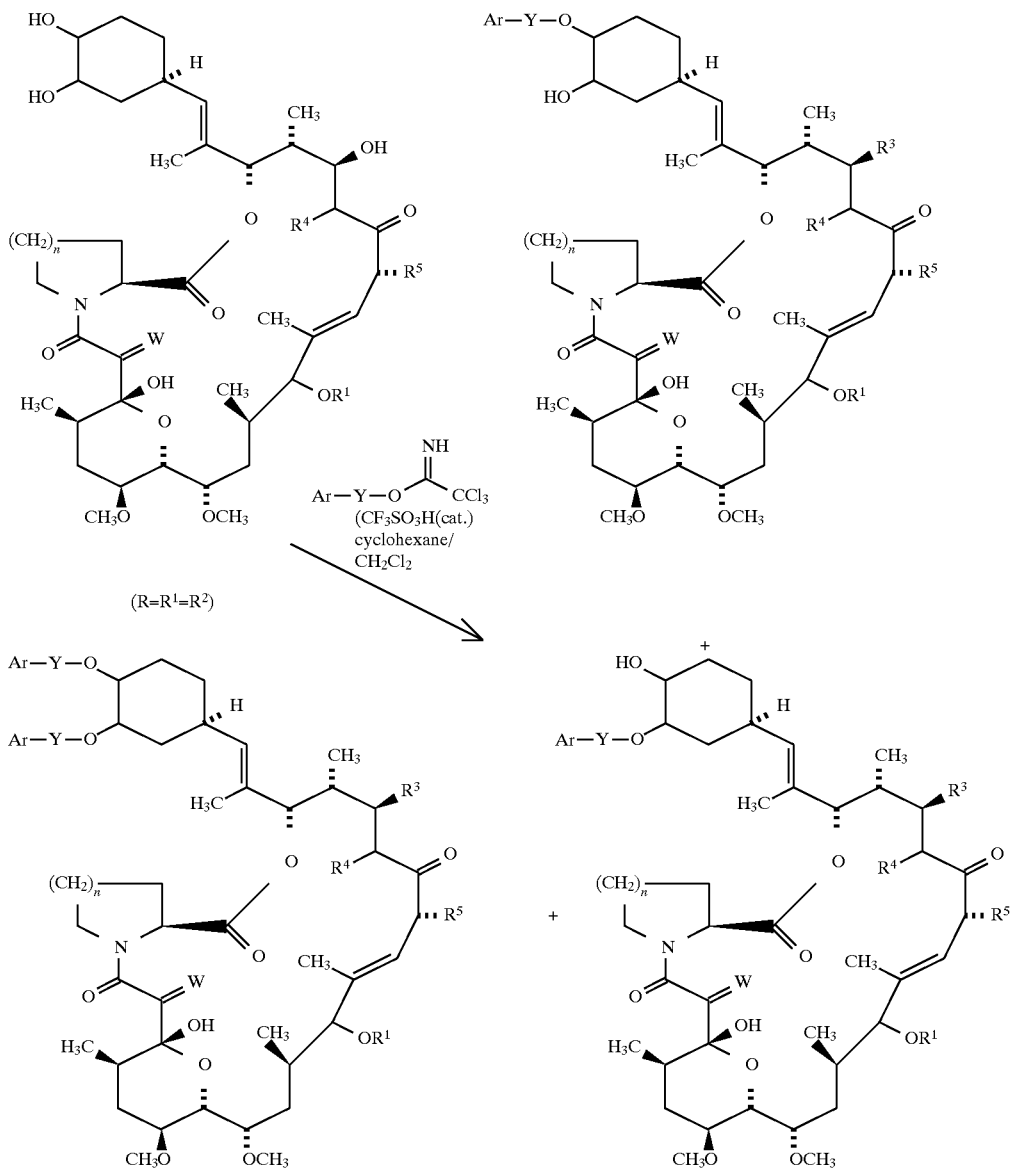

REACTION SCHEME E
REACTION SCHEME F
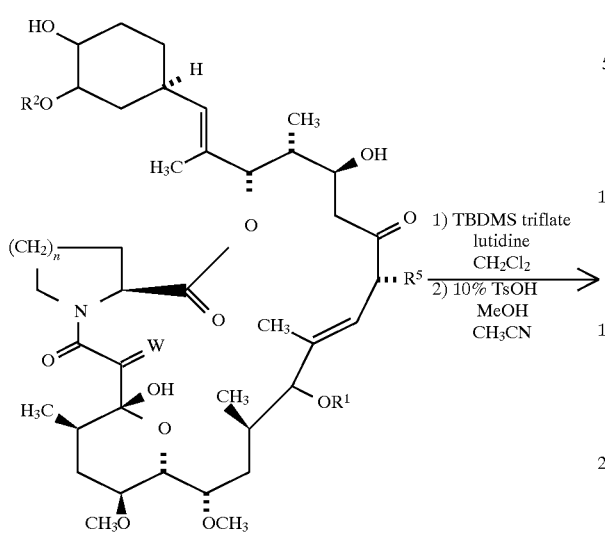
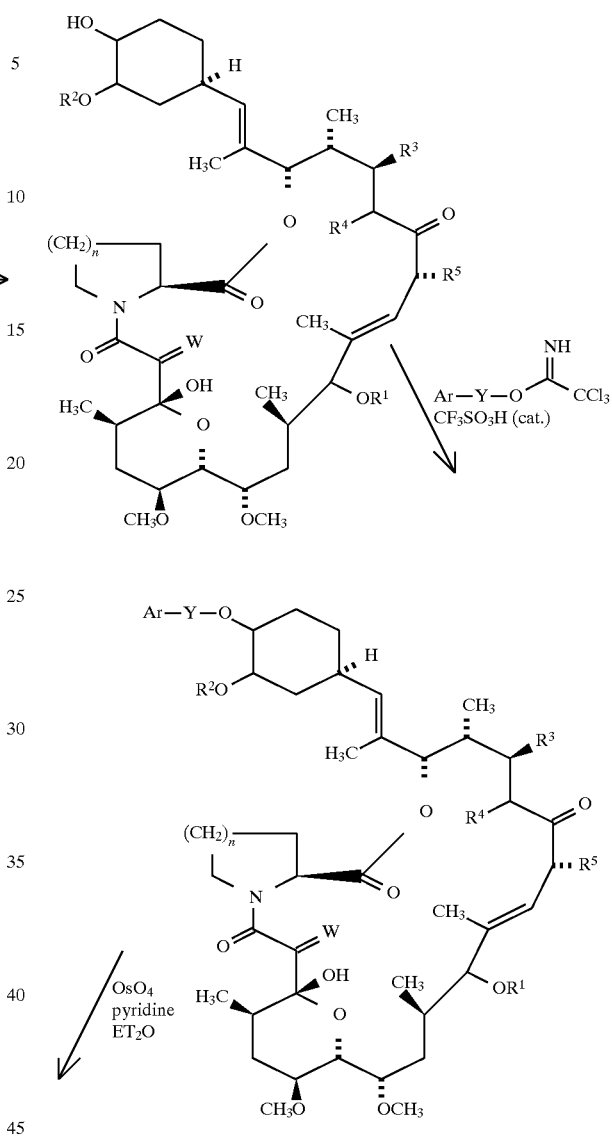

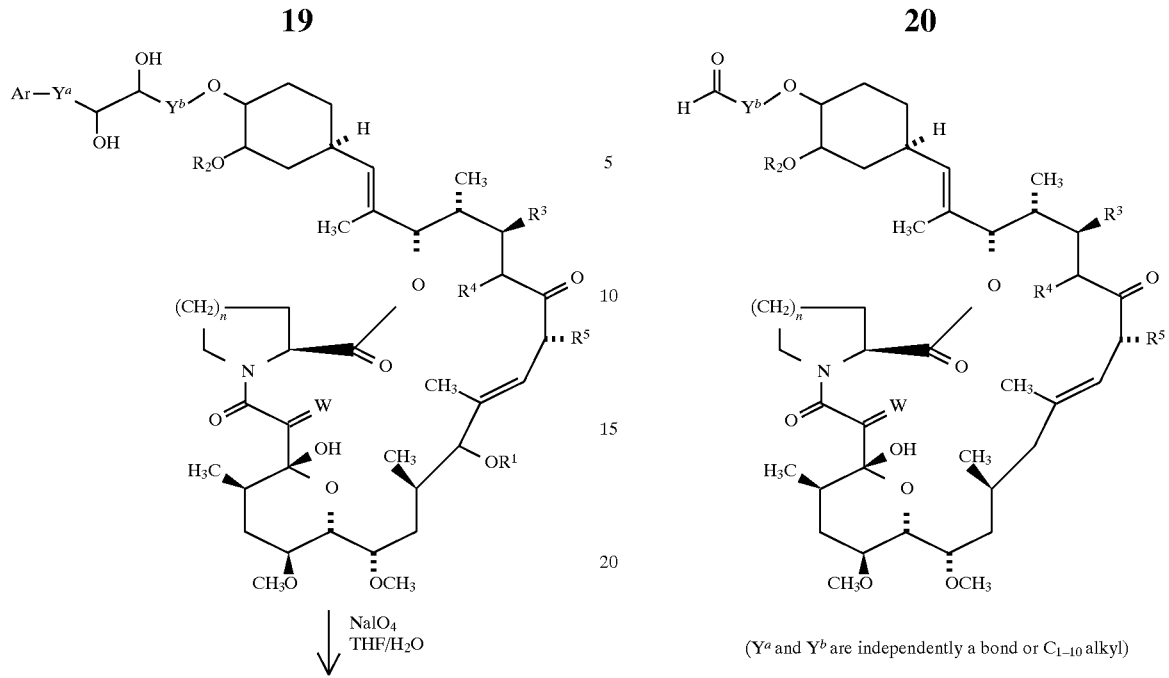
($Y^a$ and $Y^b$ are independently a bond or $C_{1-10}$ alkyl)
REACTION SCHEME G
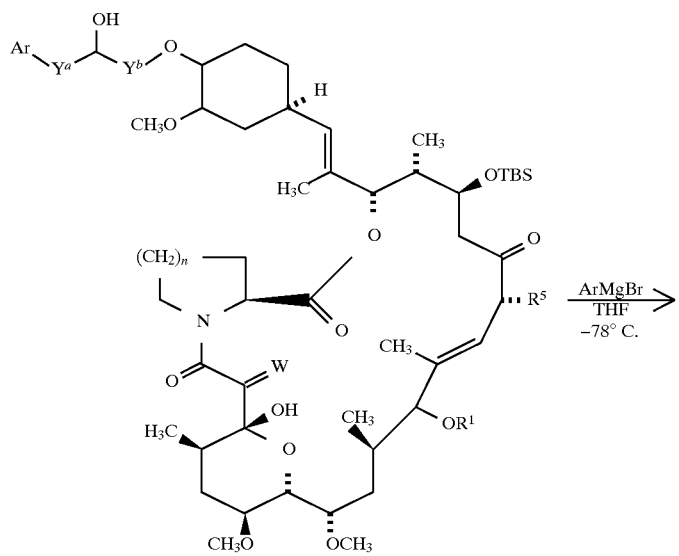

-continued
REACTION SCHEME G
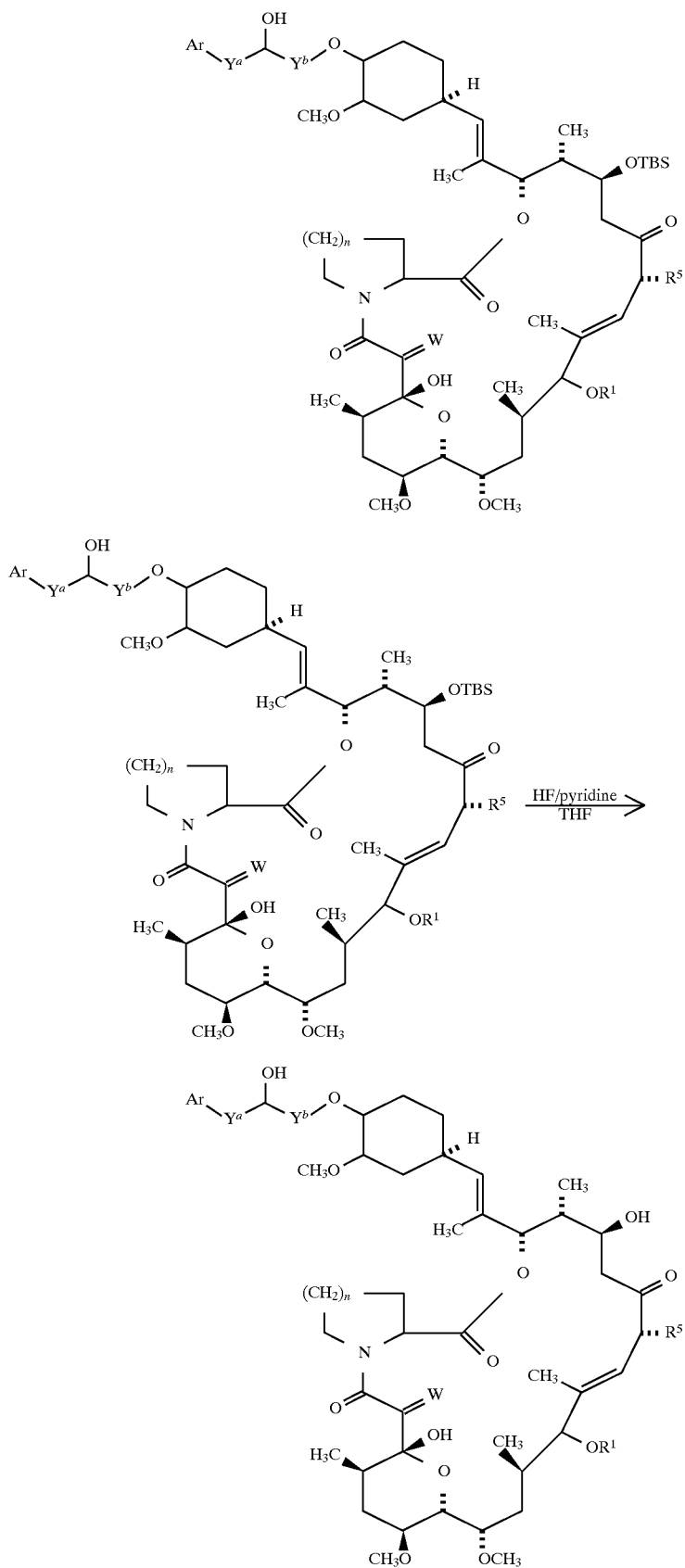

-continued
REACTION SCHEME G
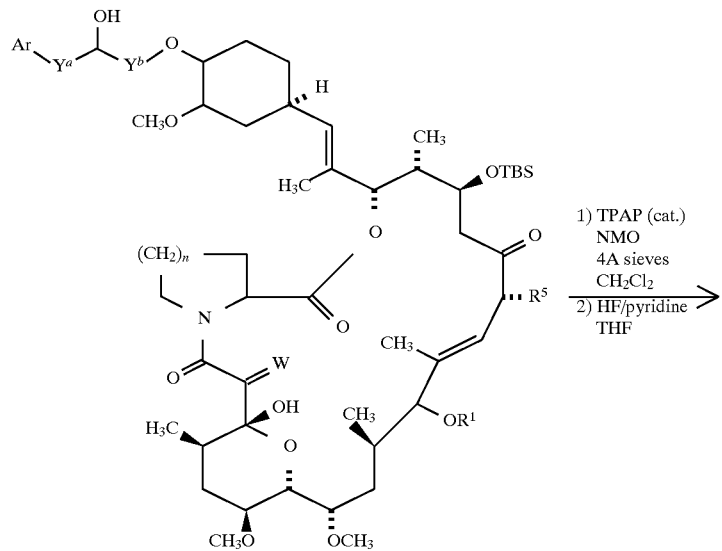
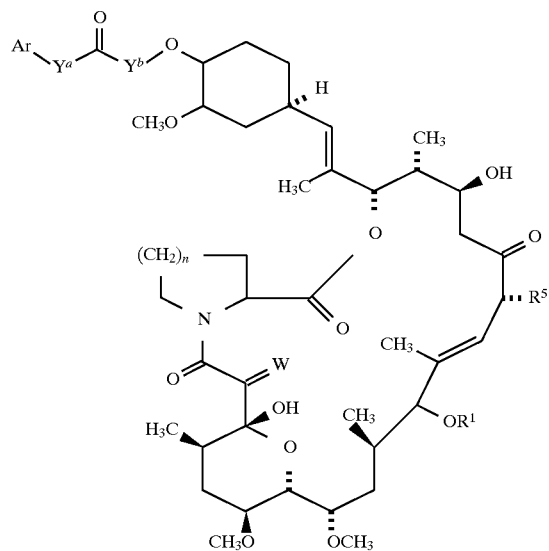

REACTION SCHEME H
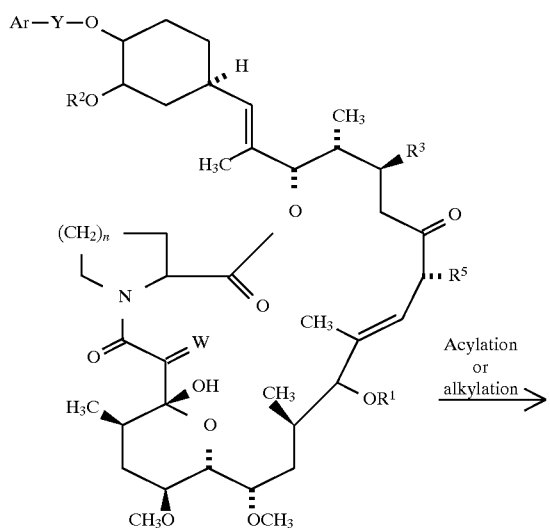
Acylation or alkylation →
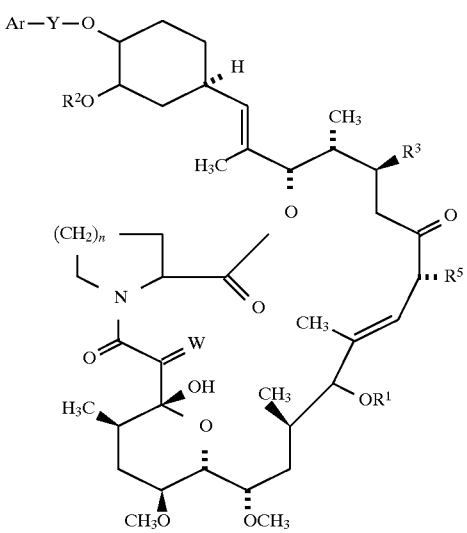
-continued
REACTION SCHEME H
REACTION SCHEME I
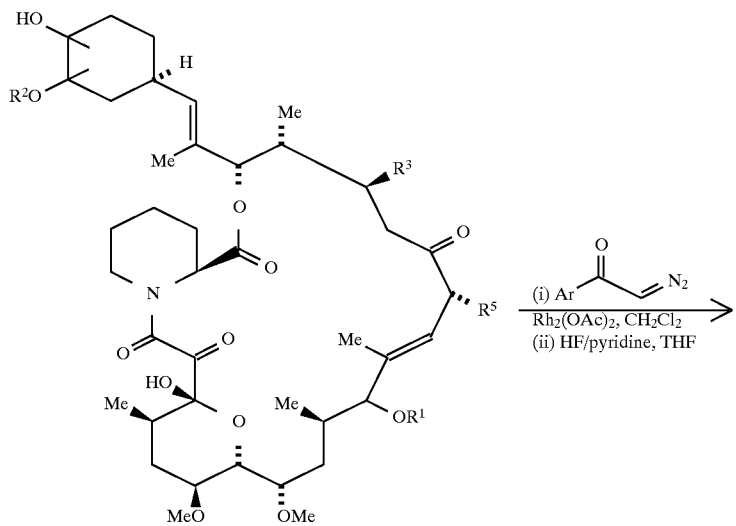
(i) Ar—C(O)—CHN$_2$, Rh$_2$(OAc)$_2$, CH$_2$Cl$_2$
(ii) HF/pyridine, THF -continued
REACTION SCHEME I
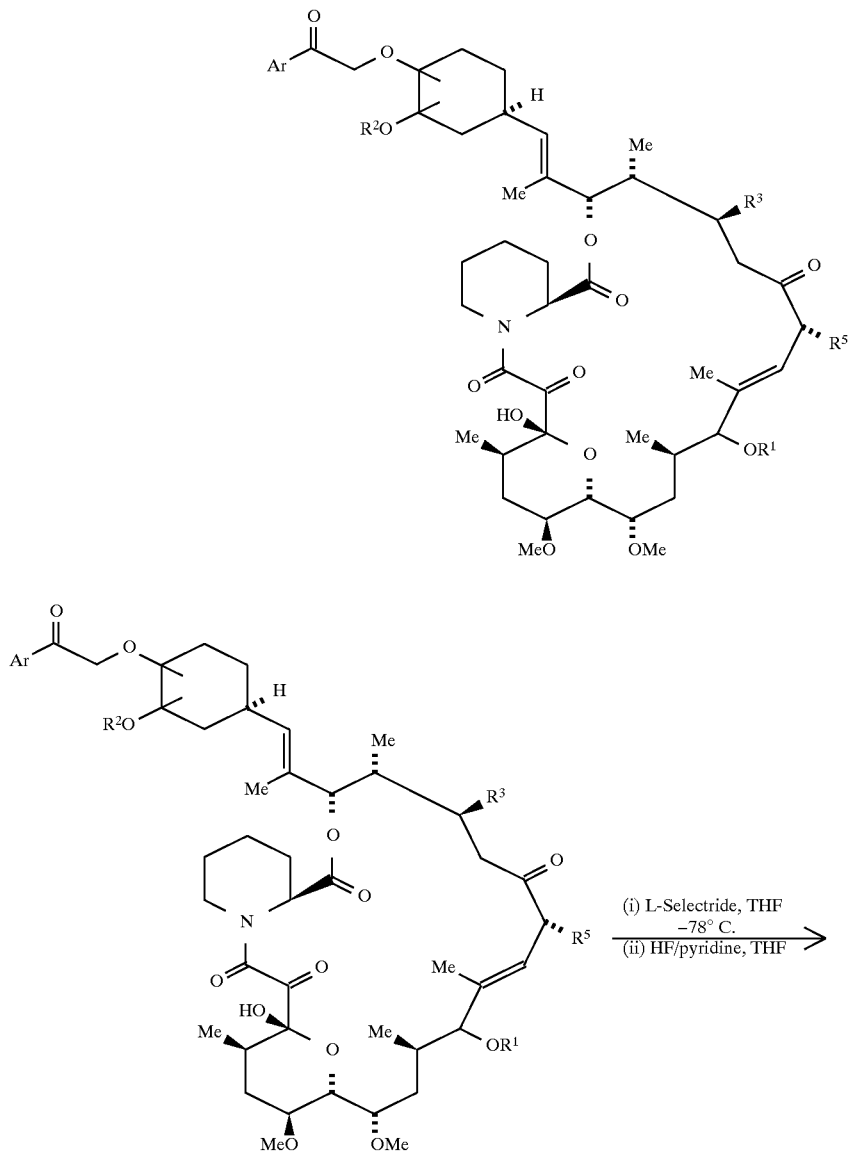

-continued
REACTION SCHEME I
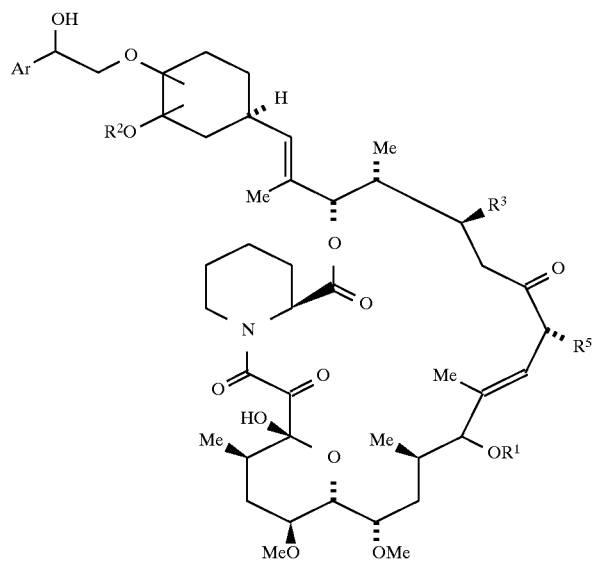
REACTION SCHEME J
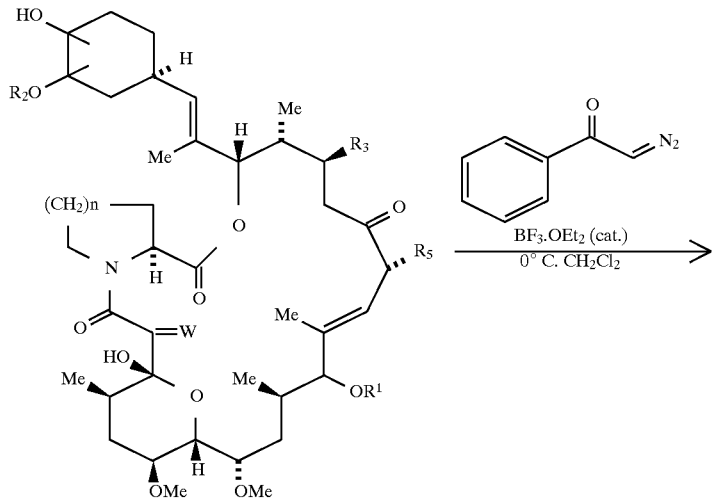

-continued
REACTION SCHEME J

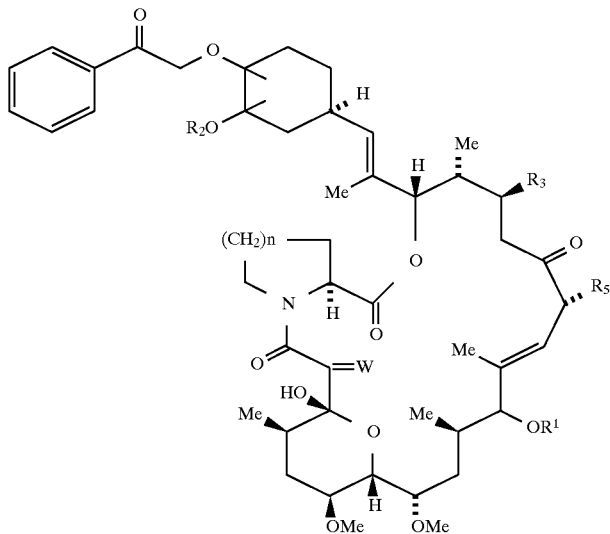

Reaction Scheme A:

As shown in Reaction Scheme A, a solution of a 4"-hydroxy-3"-methoxy macrolide in an inert organic solvent such as methylene chloride, benzene, toluene, chloroform, or the like or mixtures thereof is treated with a triarylbismuth diacetate reagent (prepared immediately prior to use by the addition of acetic acid to a suspension of a triarylbismuth carbonate in an inert organic solvent such as methylene chloride, chloroform or the like or mixtures thereof) in the presence of a catalytic amount of copper(II) acetate at a temperature of 20°–50° C., preferably room temperature, for a period of one hour to seven days, preferably one day, to give the 4"-O-aryl-3"-methoxy macrolide. Alternatively, the triarylbismuth(V) reagent can be prepared by treatment of a triarylbismuthine with a suitable oxidant such as peracetic acid, iodobenzene diacetate, bis (trifluoroacetoxy)-iodobenzene and the like in an inert solvent such as methylene chloride, chloroform, benzene, toluene and the like. The triarylbismuth(V) reagent can be used without purification or can be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D.H.E., et al., *J. Chem. Soc. Chem. Commun.,* 1986, 65 and references cited therein.

Reaction Scheme B:

Similarly, as shown in Reaction Scheme B, a solution of the 3",4"-dihydroxy macrolide is treated with a triarylbismuth diacetate reagent as described in Reaction Scheme A, to give a mixture of the 3"-hydroxy-4"-O-aryl macrolide, the 3"-O-aryl-4"-hydroxy macrolide, and the 3",4"-di-O-aryl macrolide. At this stage, the 3"-hydroxy-4"-O-aryl macrolide can be isolated from the reaction mixture using conventional methods such as column chromatography.

Reaction Scheme C:

As shown in Reaction Scheme C, a solution of the 4"-hydroxy 3"-methoxy macrolide in an inert organic solvent such as methylene chloride, chloroform, pentane, hexane, cyclohexane, heptane or the like or mixtures thereof is treated with an alkyl, alkenyl or alkynyl trichloroacetimidate reagent (prepared by the reaction of an appropriate sodium alkoxide with trichloroacetonitrile, such as described by Wessel, H. P., Iversen, T., Bundle, D. R., *J. Chem. Soc., Perkin Trans. I,* 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof at a temperature of 20°–50° C., preferably room temperature, for a period of one hour to seven days, preferably one day, to give the 4"-O-alkyl, -alkenyl or -alkynyl 3"-methoxy macrolide.

Reaction Scheme D:

Similarly, as shown in Reaction Scheme D, a solution of the 3",4"-dihydroxy macrolide in an inert organic solvent such as methylene chloride, chloroform, pentane, hexane, cyclohexane, heptane or the like or mixtures thereof is treated with an alkyl, alkenyl, or alkynyl trichloroacetimidate (prepared by the reaction of an appropriate sodium alkoxide with trichloroacetonitrile, such as described by Wessel, H. P., Iversen, T., Bundle, D. R., *J. Chem. Soc., Perkin Trans. I,* 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof of at a temperature of 20°–50° C., preferably 40° C., for a period of one hour to seven days, preferably 6 hours, to give a mixture of the 3"-O-alkyl, -alkenyl or -alkynyl 4"-hydroxy macrolide, the 3"-hydroxy 4"-O-alkyl, -alkenyl or -alkynyl macrolide and the 3",4"-di-O-alkyl,-alkenyl or -alkynyl macrolide. The desired compound can be isolated from the mixture using methods well known in the art, such as column chromatography.

Reaction Scheme E:

Protection of the C-3", C-4" and/or the C-14 hydroxy group may be accomplished by methods known in the prior art for compounds of Formula II such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like. For example, as shown in Reaction Scheme H, the C-4",14-dihydroxy C-3"-methoxy macrolide (or the C-3",4",14-trihydroxy macrolide) may be protected at C-14 as the t-butyldimethylsilyl ether by treatment with t-butyldimethylsilyl trifluoromethanesulfonate in methylene chloride to give the C-4",3"-di-O-TBDMS macrolide (or the C-3",4",14-tri-O-TBDMS macrolide). Treatment with toluenesulfonic acid in methanol results in selective removal of the C-4" silyl ether (and C-3" silyl ether, if present) to give the C-14-O-TBDMS macrolide.

Reaction Scheme F:

As shown in Reaction Scheme F, the 4"-hydroxy-3"-$R^2$O-macrolide or alternatively the 3"-hydroxy-4"-$R^1$O-macrolide (not depicted) (wherein $R^3$ is protected hydroxy or hydrogen) may be reacted with an alkenyl trichloroacetimidate (wherein $R^1$ is $C_{3-10}$ alkenyl) under conditions described in Reaction Scheme F to give the C-4"-O-alkenyl macrolide. Treatment with a stochiometric amount of osmium tetraoxide in an inert organic solvent, such as diethyl ether or tetrahydrofuran, in the presence of an amine base, such as pyridine or 4-methylmorpholine N-oxide, at or near room temperature gives the corresponding glycol (wherein A is $C_{1-8}$ alkyl). Treatment of the glycol with sodium metaperiodate in a solution of tetrahydrofuran/water gives the aldehyde. Alternatively, the alkenyl macrolide may be treated with sodium metaperiodate in the presence of a catalytic amount of osmium tetraoxide in an organic solvent to give the aldehyde directly.

Reaction Scheme G:

Hydroxy and keto derivatives may be prepared from the corresponding aldehyde as illustrated in Reaction Scheme G. The aldehyde is reacted with a nucleophilic organometallic reagent such as a Grignard reagent, an organolithium reagent, or an organocerium reagent in an organic solvent such as methylene chloride or tetrahydrofuran to give the substituted hydroxy compound. Removal of hydroxy protecting groups at other positions of the macrolide (if necessary) gives the macrolide bearing a substituted hydroxy alkoxy functionality at C-4". The alcohol may also be oxidized to the corresponding ketone by well known methods, such as with 4-methylmorpholine-N-oxide in the presence of tetrapropylammonium perruthenate catalyst under dehydrative conditions. Removal of hydroxy protecting groups (if necessary) gives the macrolide bearing a substituted keto alkoxy functionality at C-4". The procedures described in Reaction Scheme L are readily applicable to the preparation of compounds bearing analogous functionality at C-3".

Reaction Scheme H:

Hydroxy macrolides may be further derivatized by alkylation or acylation to give ether or ester derivatives by procedures well known to the practitioner of the art.

Reaction Scheme I:

As illustrated in Scheme N, the hydroxy macrolide may be derivatized by treatment with a substituted alpha-diazoketone in an inert organic solvent such as methylene chloride in the presence of a catalyst such as rhodium acetate to provide the corresponding ether adduct. The ketone functionality of the appended ether may be selctively reduced in an inert organic solvent such as diethyl ether or tetrahydrofuran at −78° C. by treatment with a reducing agent, such as L-Selectride, potassium triphenlyborohydride, diisobutyl aluminum hydride or lithium triethylborohydride.

Reaction Scheme J:

Alternatively, as shown in Scheme O, treatment of the hydroxy macrolide with a substituted 2-diazoacetophenone in an inert organic solvent such as methylene chloride with a Lewis acid catalyst such as boron trifluoride etherate provides the corresponding ether adduct.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (See for example, *J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31 3283,3287).

The compounds of the present invention are capable of forming salts with various inorganic and organic acids and bases and such salts are also within the scope of this invention. Examples of such acid addition salts (which are negative counterions defined herein as M−) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as M+) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne Alopecia areata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratitis, herpetic keratitis, conical cornea, dystorphia epithelialis corneae, corneal leukoma, ocular pemphigus, Mooren's ulcer, Scleritis, Graves' ophthalmopathy, severe intraocular inflammation, and the like.

The compounds of Formula I are also useful for treating multidrug resistance of tumor cells, (i.e. enhancing the activity and/or sensitivity of chemotherapeutic agents), preventing or treating inflammation of mucosa or blood vessels (such as leukotriene B4-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis), or intestinal lesions associated with thermal burns, cytomegalovirus infection, particularly HCMV infection.

Further, the compounds of Formula I are also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung, and idiopathic interstitial pneumonia; skin diseases including dermato-myositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the invention are also indicated for use as antimicrobial agents, and thus may be used in the treatment of diseases caused by pathogenic microorganisms and the like.

The compounds of Formula I may also be useful in the prevention or treatment of immunodepression (such as AIDS, HIV infection, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings,* 1987, *XIX,* Supp. 6, 17–22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

For modifying the activity and/or toxicity of FK-506-type immunosuppressants, a compound of Formula I may be administered prior to, in conjuction with or subsequent to the administration of an FK-506-type of a compound.

The compounds of Formula I may optionally be employed in co-therapy with anti-proliferative agents. Particularly preferred is co-therapy with an antiproliferative agent selected from the group consisting of azathioprine (AZA), brequinar sodium, deoxyspergualin (DSG), mizaribine, mycophenolic acid morpholino ester (RS-61443), cyclosporin and rapamycin.

The compounds of Formula I may also be employed in conjunction with (or in a pharmaceutical composition additionally comprising):

(1) a 5α-reductase inhibitor,
(2) a cyclosporin,
(3) a potassium channel opener (such as minoxidil), or
(4) a phospholipid.

Such co-therapy is particularly useful in hair revitalizing, such as in the treatment of male pattern alopecia, female pattern alopecia, alopecia senilis or alopecia areata, by providing epilation prevention, hair germination, and/or a promotion of hair generation and hair growth.

Such co-therapy is further useful in treating the hyperandrogenic conditions of androgenic alopecia, acne vulgaris, seborrhea, and female hirsutism.

For co-therapy of these conditions and diseases a compound of Formula I may be administered in combination with prior to, concurrent to, or subsequent to the administration of other agent(s).

For hair revitalizing the compound of Formula I may be administered topically or orally. Cyclosporin may be administered topically or orally. Although the 5α-reductase inhibitor or the potassium channel opener may be administered topically or orally, it is preferable that it be administered topically to the scalp. For unitary formulation, however, the preferred mode of administration is topically. It is especially preferred that the hair revitalizing composition of the present invention is administered by a percutaneous administration or by spraying onto the skin.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

17-Ethyl-1,14,20-trihydroxy-12-[2'-(4"-(naphth-2-yloxy)-3"-methoxycyclohexyl)-1'-methylvinyl] -23, 25-dimethoxy-13,19,21,27-tetramethyl-11,28-dioxa-4-aza-tricyclo-[22.3.1.0$^{4,9}$]octacos-18-ene-2,3,10,16-tetraone To a stirred solution of tri(2-naphthyl)bismuthine (100 mg., 0.169 mmol, 1.38 eq.) in $CH_2Cl_2$ (2 mL.) and THF (650 μL.) was added peracetic acid (44 μL., 0.209 mmol., 1.7 eq. 32% solution in dilute HOAc). After 5 minutes 17-ethyl-1, 14,20-trihydroxy-12-[2'-(4"-hydroxy-3"-methoxycyclohexyl)-1"-methylvinyl]-23,25-dimethoxy-13, 19,21,27-tetramethyl-11,28-dioxa-4-aza-tricyclo-[22.3.1.0$^{4,9}$]-octacos-18-ene-2,3,10,16-tetraone (100 mg., 0.123 mmol., 1 eq.) was added, followed by addition of $Cu(OAc)_2$ (10 mg., 0.055 mmol., 0.45 eq.). The mixture was stirred at room temperature overnight. The reaction was quenched with saturated aqueous $NaHCO_3$ and extracted 4× with $CH_2Cl_2$ The organic extracts were combined, dried over anhydrous $Na_2SO_4$, filtered and concentrated in vacuo. The product was purified by preparative TLC (2×0.5 mm ptlc plates eluted with 2:1 hexanes/acetone) giving 51 mg of the title compound.

Using the methodolgy described in Reaction Scheme 1 and also described in Example 1 the following compounds (Examples 2–14) can be prepared:

17-ethyl-1,14,20-trihydroxy-12-[2'-(4"-phenyloxy-3"-methoxycyclohexyl)-1'-methylvinyl]-23,25-dimethoxy-13,19,21,27-tetramethyl-11,28-dioxa-4-aza-tricyclo-[22.3.1.0$^{4,9}$]octacos-18-ene-2,3,10,16-tetraone 17-ethyl-1,14,20-trihydroxy-12-[2'-(4"-(4'"-methoxyphenyloxy))-3"-methoxycyclohexyl)-1'-methylvinyl]-23,25-dimethoxy-13,19,21,27-tetramethyl-11,28-dioxa-4-aza-tricyclo-[22.3.1.0$^{4,9}$]octacos-18-ene-2,3,10,16-tetraone 17-ethyl-1,14,20-trihydroxy-12-[2'-(4"-(6'"-methoxynaphth-2'"-yloxy)-3"-methoxycyclohexyl)-1'-methylvinyl]-23,25-dimethoxy-13,19,21,27 -tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(naphth-1-yloxy)-3"-methoxycyclohexyl)-1'-methylvinyl] -23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(4'"-fluorphenyloxy)-3"-methoxycyclohexyl)-1'-methylvinyl] -23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(4'"-chlorophenyloxy)-3"-methoxycyclohexyl)-1'-methylvinyl]-23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(4'"-methylphenyloxy)-3"-methoxycyclohexyl)-1'-methylvinyl]-23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(4'"-phenoxyphenyloxy)-3"-methoxycyclohexyl)-1'-methylvinyl]-23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(3'"-methoxyphenyloxy)-3"-methoxycyclohexyl)-1'-methylvinyl]-23,25-dimethoxy-13,19,21,27-tetramethyl-11,28-dioxa-4-aza-tricyclo-[22.3. 1.0$^{4,9}$]octacos-18-ene-2,3,10,16-tetraone 17-ethyl-1,14,20-trihydroxy-12-[2'-(4"-(3'"-methylphenyloxy)-3"-methoxycyclohexyl)-1'-methylvinyl]-23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(4'"-hydroxyphenyloxy)-3"-methoxycyclohexyl)-1'-methylvinyl]-23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(4'"-dimethylaminophenyloxy)-3"-methoxycyclohexyl)-1'-methylvinyl]-23,25-dimethoxy-13,19,21,27-tetramethyl-11,28-dioxa-4-aza-tricyclo-[22.3.1 .0$^{4,9}$]octacos-18-ene-2,3,10,16-tetraone 17-ethyl-1,14,20-trihydroxy-12-[2'-(4"-(2'",3'"-dihydrobenzofuran-5-yloxy)-3"-methoxycyclohexyl)-1'-methylvinyl]-23,25-dimethoxy-13,19,21,27-tetramethyl-11,28-dioxa-4-aza-tricyclo-[22.3.1.0$^{4,9}$]octacos-18-ene-2,3,10,16-tetraone 17-ethyl-1,14,20-trihydroxy-12-[2'-(4"-(3'",4'"-methylendioxyphenyloxy)-3"-methoxycyclohexyl)-1'-methylvinyl]-23,25-dimethoxy-13,19,21,27-tetramethyl-11,28-dioxa-4-aza-tricyclo-[22.3.1 .0$^{4,9}$]octacos-18-ene-2,3,10,16-tetraone

EXAMPLE 15

T-Cell Proliferation Assay

1. Sample Preparation

The compounds to be assayed were dissolved in absolute ethanol at 1 mg/ml.

2. Assay

Spleens from C57B 1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at 2.5×10$^5$ cells/ml in complete culture medium composed of RPMI 1640 medium with 10% heat- inactivated fetal calf serum, 100 mM glutamine, 1 mM sodium pyruvate, 2×10$^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. The compound 17-allyl-1,14-dihydroxy-12-[2'-(4"-hydroxy-3"-methoxycyclohexyl)-1'-methylvinyl]-23,25-dimethoxy-13, 19,21,27-tetramethyl-11,28-dioxa-4-azatricyclo[22.3.1.0$^{4,9}$] octacos-18-ene-2,3,10,16-tetraone was used as a standard. The culture plates were then incubated at 37° C. in a humidified atmosphere of 5% CO$_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

The results of this assay are representative of the intrinsic immunosuppressive activity of the compounds of the present invention.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

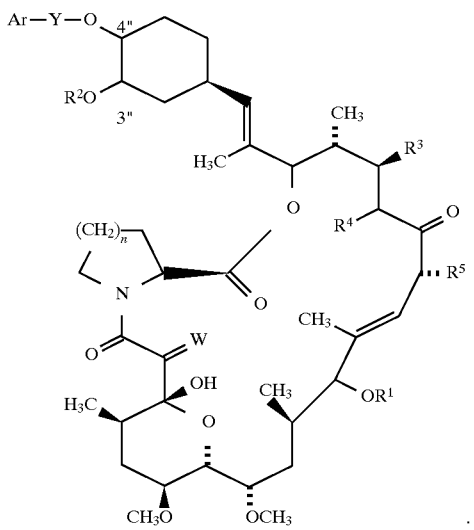

What is claimed is:

1. A compound having the formula

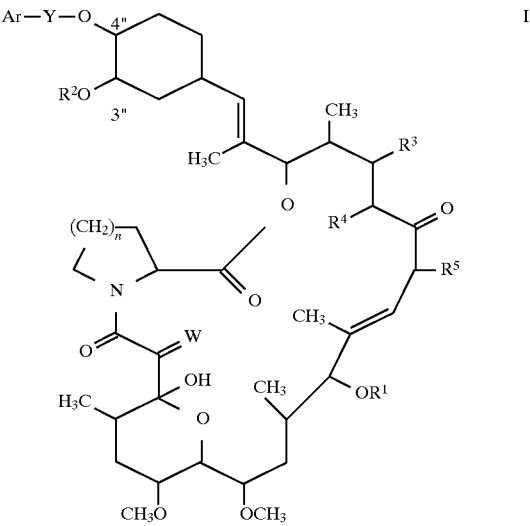

or a pharmaceutically acceptable salt thereof, wherein:

Ar is phenyl, naphthyl or biphenyl, each optionally substituted with 1 to 3 groups independently selected from X, $R^1$ is hydrogen, $C_{1-6}$ alkyl, $C_{1-6}$ alkanoyl, aroyl or aryl-$C_{1-6}$ alkanoyl;

$R^2$ is hydrogen or methyl;

$R^3$ is hydrogen or —$OR^1$;

$R^4$ is hydrogen, or $R^3$ and $R^4$ taken together form a double bond;

$R^5$ is methyl, ethyl, propyl or allyl;

W is O or (H, OH);

X is:
- (b) $C_{1-7}$ alkyl,
- (c) $C_{2-6}$ alkenyl,
- (d) halogen,
- (e) —$(CH_2)_m$—$NR^6R^7$, wherein $R^6$ and $R^7$ are independently hydrogen or C1–10 alkyl, or R6, R7 and the nitrogen atom to which they are attached together form an unsubstituted or substituted 3–7-membered saturated heterocyclic ring which can include one or two additional heteroatoms independently selected from the group consisting of O, $S(O)_m$, $NR^{14}$, wherein $R^{14}$ is hydrogen or $C_{1-6}$ alkyl, and m is 0 to 2,
- (f) —CN,
- (g) —CHO,
- (h) —$CF_3$,
- (i) —$S(O)_mR^8$, wherein $R^8$ is hydrogen, $C_{1-6}$alkyl, trifluoromethyl, or phenyl, and m is as defined above,
- (l) —$CONR^6R^7$, wherein $R^6$ and $R^7$ are as defined above,
- (m) $R^9O(CH_2)_m$— wherein $R^9$ is hydrogen, $C_{1-3}$ alkyl, hydroxy-$C_{2-3}$alkyl, trifluoromethyl, phenyl or naphthyl and m is as defined above,
- (n) —$CH(OR^{12})(OR^{13})$, wherein $R^{12}$ and $R^{13}$ are $C_{1-3}$ alkyl or taken together form an ethyl or propyl bridge,
- (o) $R^9C(O)O(CH_2)_m$— wherein $R^9$ and m are as defined above, and
- (p) $R^9OC(O)(CH_2)_m$— wherein $R^9$ and m are as defined above, and
- (q) —$OR^8$;

or any two adjacent X can be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl;

Y is a bond; and n is 1 or 2, or a pharmaceutically acceptable salt thereof.

2. A compound of claim 1 wherein
Ar is phenyl or naphthyl, each optionally substituted with 1 to 3 groups independently selected from X; and
Y is a bond.

3. A compound of claim 1 wherein
$R^5$ is ethyl or allyl.

4. A compound of claim 1 wherein
Ar is phenyl or naphthyl, each optionally substituted with 1 to 3 groups independently selected from X;
$R^3$ is hydrogen or OH;
$R^4$ is hydrogen;
$R^5$ is ethyl or allyl;
W is O;
Y is a bond;
n is 2.

5. A pharmaceutical composition which comprises a therapeutically effective amount of a compound of claim 1 and a pharmaceutically acceptable carrier.

6. A method for the treatment of immunoregulatory disorders or diseases comprising administering to a mammalian species in need of such treatment of an effective amount of a compound of claim 1.

7. A method for the treatment of resistance to transplantation comprising administering to a mammalian species in need of such treatment of an effective amount of a compound of claim 1.

8. A compound of claim 1 having the stereochemistry as shown below: